(12) United States Patent
Rock et al.

(10) Patent No.: US 11,560,651 B2
(45) Date of Patent: Jan. 24, 2023

(54) COMPRESSION FABRICS WITH TAILORED COMFORT

(71) Applicant: Myant Capital Partners Inc., Toronto (CA)

(72) Inventors: Moshe Rock, Brookline, MA (US); Vikram Sharma, Melrose, MA (US)

(73) Assignee: MYANT CAPITAL PARTNERS INC., Toronto (CA)

( * ) Notice: Subject to any disclaimer, the term of this patent is extended or adjusted under 35 U.S.C. 154(b) by 0 days.

(21) Appl. No.: 16/259,452

(22) Filed: Jan. 28, 2019

(65) Prior Publication Data
US 2019/0352814 A1 Nov. 21, 2019

Related U.S. Application Data

(63) Continuation of application No. 14/851,408, filed on Sep. 11, 2015, now abandoned.
(Continued)

(51) Int. Cl.
*D04B 1/18* (2006.01)
*A61F 13/08* (2006.01)
(Continued)

(52) U.S. Cl.
CPC ............ *D04B 1/18* (2013.01); *A41D 13/0015* (2013.01); *A61F 13/08* (2013.01); *D04B 1/265* (2013.01);
(Continued)

(58) Field of Classification Search
CPC .. D04B 1/18; D04B 1/26; D04B 1/265; A61F 13/08
See application file for complete search history.

(56) References Cited

U.S. PATENT DOCUMENTS

| | | | | |
|---|---|---|---|---|
| 2,574,873 A | * | 11/1951 | Jobst | A61F 13/08 602/63 |
| 4,180,065 A | * | 12/1979 | Bowen | A61F 13/08 2/239 |

(Continued)

FOREIGN PATENT DOCUMENTS

| | | | | |
|---|---|---|---|---|
| GB | 2260686 A | * | 4/1993 | A61F 13/08 |
| WO | WO-2011143489 A2 | * | 11/2011 | A61F 13/08 |

OTHER PUBLICATIONS

CIPO, Office Action for CA Application No. 2904034 dated Oct. 20, 2021.

*Primary Examiner* — Megan E Lynch
(74) *Attorney, Agent, or Firm* — Norton Rose Fulbright Canada LLP

(57) ABSTRACT

Certain embodiments according to the invention provide compression articles suitable for a wide variety of uses (e.g., compression socks, athletic garments, etc.). In accordance with certain embodiments, the compression article includes at least two uniform compression regions, including a first uniform compression region having a first compression pressure and a second uniform compression region having a second compression pressure, and at least one transitioning compression region, including a first transitioning compression region positioned between the first and second uniform compression regions. The first transitioning compression region comprises a first end adjacent or proximate to the first uniform compression region and a second end adjacent or proximate to the second uniform compression region. The first transitioning compression region comprises a compression pressure gradient extending from the first end to the second end of the first transitioning compression region.

16 Claims, 13 Drawing Sheets

Related U.S. Application Data

(60) Provisional application No. 62/070,960, filed on Sep. 11, 2014.

(51) Int. Cl.
  A41D 13/00 (2006.01)
  D04B 1/26 (2006.01)
  A41D 31/00 (2019.01)
  A41D 13/12 (2006.01)

(52) U.S. Cl.
  CPC .......... *A41D 13/1236* (2013.01); *A41D 31/00* (2013.01); *A41D 2400/38* (2013.01); *D10B 2509/028* (2013.01)

(56) References Cited

U.S. PATENT DOCUMENTS

| | | | | |
|---|---|---|---|---|
| 4,502,301 A * | 3/1985 | Swallow | | A61F 13/08 602/62 |
| 4,522,044 A * | 6/1985 | Lineberry | | A41B 11/02 66/185 |
| 4,561,267 A * | 12/1985 | Wilkinson | | D04B 1/26 66/172 E |
| 5,898,948 A * | 5/1999 | Kelly | | A41B 11/00 2/239 |
| 6,012,177 A * | 1/2000 | Cortinovis | | A61F 13/08 2/239 |
| 6,123,681 A * | 9/2000 | Brown, III | | A61H 23/02 2/239 |
| 7,669,252 B2 * | 3/2010 | Wei | | A41B 11/08 2/239 |
| 7,895,863 B2 * | 3/2011 | Smith | | D02G 3/328 66/172 E |
| 2006/0247566 A1 * | 11/2006 | Gobet | | A61F 13/08 602/62 |
| 2007/0283483 A1 * | 12/2007 | Jacober | | D04B 1/265 2/239 |
| 2009/0234265 A1 * | 9/2009 | Reid, Jr. | | A61H 9/0078 602/61 |
| 2010/0137776 A1 * | 6/2010 | Virkus | | A61F 13/08 602/62 |
| 2011/0257575 A1 * | 10/2011 | Farrow | | A61F 13/08 602/75 |
| 2012/0024014 A1 * | 2/2012 | Fukui | | D04B 15/06 66/171 |
| 2012/0102613 A1 * | 5/2012 | Loth | | A41D 13/0543 2/22 |
| 2012/0102625 A1 * | 5/2012 | Klein | | D04B 1/04 2/239 |
| 2012/0180195 A1 * | 7/2012 | Shull | | D04B 1/18 2/239 |
| 2013/0172926 A1 * | 7/2013 | Barker | | A61F 13/08 606/201 |
| 2013/0178779 A1 * | 7/2013 | Duda | | A41D 11/00 602/48 |
| 2014/0058311 A1 * | 2/2014 | Higgins | | A61F 13/064 602/63 |
| 2014/0128785 A1 * | 5/2014 | Dickson | | A61H 1/008 601/84 |
| 2015/0051524 A1 * | 2/2015 | Messier | | A61F 13/08 601/84 |
| 2015/0157524 A1 * | 6/2015 | Reid, Jr. | | A61F 13/06 601/84 |
| 2016/0038346 A1 * | 2/2016 | Collins | | A41B 11/08 602/63 |

* cited by examiner

☒KNIT ⊡TUCK ☐MISS

COMPRESSION FABRICS WITH TAILORED COMFORT

CROSS-REFERENCE TO RELATED APPLICATIONS

This application claims the benefit of U.S. Provisional Application No. 62/070,960 filed on Sep. 11, 2014, the entire contents of which are hereby incorporated herein by reference.

TECHNICAL FIELD

The presently-disclosed invention relates generally to compression fabrics and more particularly to compression articles made with such compression fabrics to provide tailored comfort and/or a tailored compression pressure profile along the length of such compression articles.

BACKGROUND

For medical applications, the application of inlay stretch yarn or plated stretch yarn and a laid-in stitch in a compression garment may provide a desired compression "dosage" for preventative and therapeutic purposes. Most medical compression garments are individually designed and manufactured for a particular part of the body, such as stockings, gloves, sleeves, face masks, and body suits, and are worn for an appointed time depending on the medical treatment need. For example, compression stockings have been used in therapeutic management of varicose veins, venous thrombosis, lymphedema, poor blood circulation, muscle fatigue and/or the like. In addition, compression garments have also been used to provide compression on the body's muscles to increase blood flow to improve performance, reduce injury risk, and accelerate muscle recovery during and after exercise. Moreover, compression garments are increasingly used as shapewear to enhance body image by creating attractive contours, reducing abdominal size and/or the like.

The circumference of a compression garment is smaller than the size of the body part on which it is to be used so that the garment stretches when placed on that body part in order to provide optimum compression. The level of compression is governed by the garment size as well as the amount of fabric that stretches. Standard compression garments apply different levels of compression to different segments of the garment. However, this approach creates an abrupt change in compression moving between different sections of the garment. These abrupt changes make it difficult to put on and take off the garment because it can cause discomfort and/or pain, particularly for the elderly or handicapped individuals. Moreover, in some scenarios, standard compression garments may even restrict circulation by bunching or tightening at the seams, particularly at the foot, toe, ankle, or lower leg area. In this regard, standard compression articles are difficult to use and may even exacerbate medical problems.

Therefore there at least remains a need in the art for compression garments that provide a contoured fit having smooth transitions from one area of compressive pressure to another.

BRIEF SUMMARY

One or more embodiments of the invention may address one or more of the aforementioned problems. Certain embodiments according to the invention provide compression articles suitable for a wide variety of uses (e.g., compression socks, athletic garments, shapewear, etc.). In accordance with certain embodiments, the compression article has at least two uniform compression regions, including a first uniform compression region having a first compression pressure and a second uniform compression region having a second compression pressure, and at least one transitioning compression region, including a first transitioning compression region positioned between the first and second uniform compression regions. The first transitioning compression region, according to certain embodiments, may comprise a first end adjacent or proximate to the first uniform compression region and a second end adjacent or proximate to the second uniform compression region. The first transitioning compression region comprises a compression pressure gradient extending from the first end to the second end of the first transitioning compression region, in which the first end to the transition compression region comprises a greater compression pressure than the second end of the transition compression region.

In another aspect, certain embodiments of the invention provide a method for making a seamless compression article. In accordance with certain embodiments, the method includes forming at least a first uniform compression region comprising a first compression pressure, forming a first transitioning compression region adjacent or proximate to the first uniform compression region, said first transitioning compression region comprising a first end adjacent or proximate to the first uniform compression region and a second end, and forming a second uniform compression region adjacent or proximate to the second end of the first transitioning compression region, the second uniform compression region comprising a second compression pressure being different from the first compression pressure. In such embodiments, the first transitioning compression region is located between the first uniform compression region and the second uniform compression region, and the first transitioning compression region comprises a compression pressure gradient extending from the first end to the second end of the first transitioning compression region.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
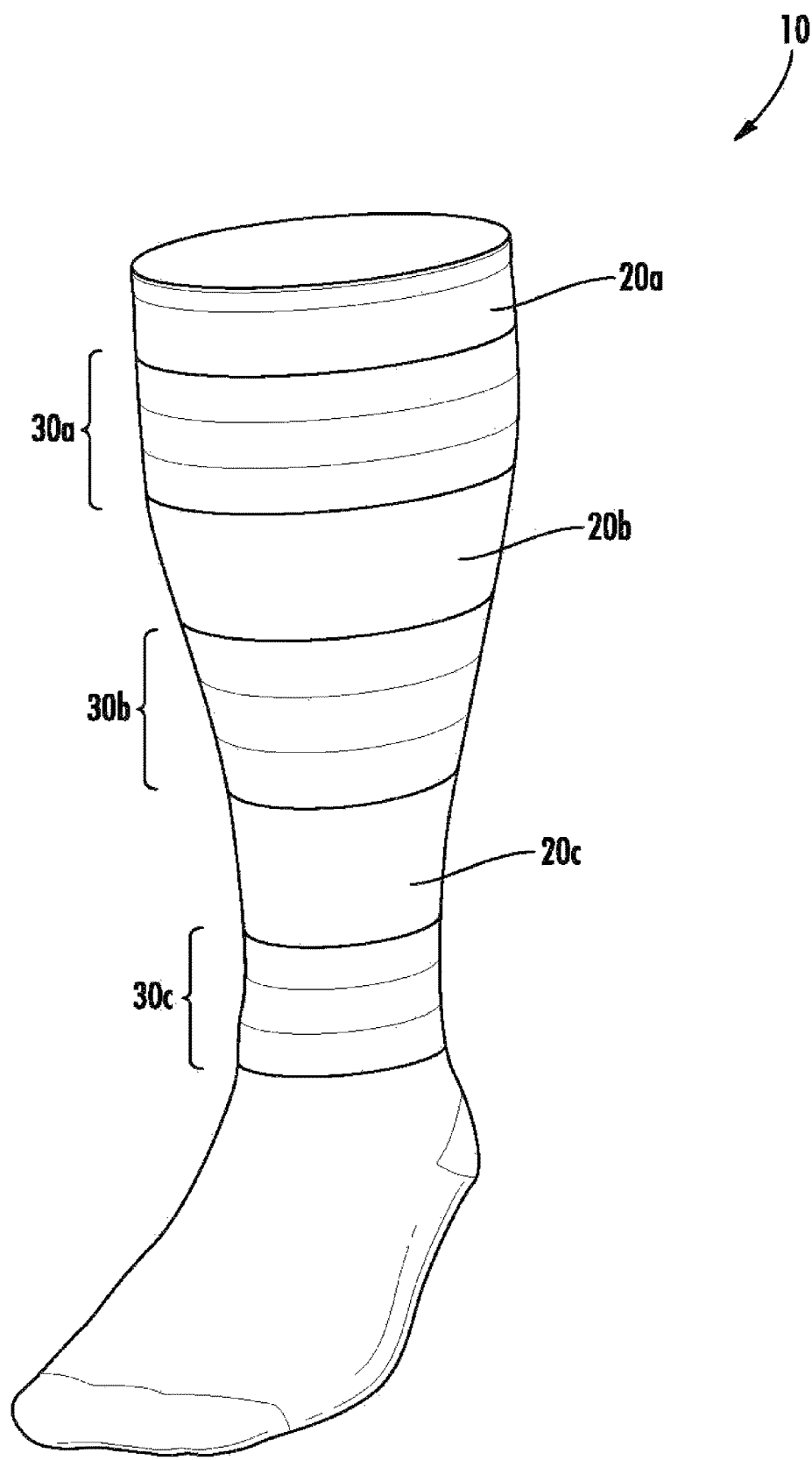
FIG. 1 illustrates a perspective view of a compression article according to an example embodiment.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In accordance with certain embodiments, the invention includes a compression article suitable for a wide variety of uses (e.g., compression socks, athletic garments, shapewear, etc.). Compression articles, according to certain embodiments, may include at least two uniform compression regions, including a first uniform compression region having a first compression pressure and a second uniform compression region having a second compression pressure. Such embodiments may also include at least one transitioning compression region, which may include a first transitioning compression region positioned between the first and second uniform compression regions. In accordance with certain embodiments, the first transitioning compression region may comprise a first end adjacent or proximate to the first uniform compression region and a second end adjacent or proximate to the second uniform compression region. The first transitioning compression region may comprise a compression pressure gradient extending from the first end to the second end of the first transitioning compression region, in which the first end to the transition compression region comprises a greater compression pressure than the second end of the transition compression region. In this regard, the compression pressure provided by the article along the length of the transitioning compression regions (e.g., the first transitioning compression region) may be non-uniform. The transitioning compression regions, for example, may be configured such that a gradual compression gradient along the length of the transition regions minimizes any undesirable abrupt changes in compression pressure along the length of the compression article. In certain embodiments, for example, the first compression region may comprise a first compression pressure that is reasonably greater in magnitude than the second compression pressure associated with the second uniform compression region. In such embodiments, for example, the first transitioning region being located between the first and second uniform compression regions provides a graded pressure (e.g., a gradient pressure profile) to minimize or eliminate any abrupt change in compression pressure between the first and second uniform compression regions. As described below, compression articles according to certain embodiments may comprise or generally provide a tailored compression profile along the length of the compression article by, at least in part, incorporating one or more transitioning compression regions along the length of the compression fabric. In accordance with certain embodiments, the compression article may comprise a seamless compression article (e.g., devoid of seams).

In one aspect, the invention provides compression articles suitable for a wide variety of uses (e.g., compression socks, athletic garments, shapewear, etc.). FIG. 1 illustrates a perspective view of a compression article according to an example embodiment. In accordance with certain embodiments, the compression article 10 includes at least two uniform compression regions. In the particular embodiment illustrated in FIG. 1, the compression article 10 includes three separate uniform compression regions 20*a*, 20*b*, 20*c*, including a first uniform compression region 20*a* having a first compression pressure, a second uniform compression region 20*b* having a second compression pressure, and a third uniform compression region 20*c* having a third compression pressure, in which at least the second compression pressure is different from at least one of the first compression pressure or the third compression pressure. The compression article 10 also comprises at least one transitioning compression region 30*a*, 30*b*, 30*c*, including a first transitioning compression region 30*a* positioned between the first and second uniform compression regions 20*a*, 20*b*. The first transitioning compression region 30*a* comprises a first end adjacent or proximate to the first uniform compression region 20*a* and a second end adjacent or proximate to the second uniform compression region 20*b*. The first transitioning compression region 30*a*, for instance, may comprise a compression pressure gradient extending from the first end to the second end of the first transitioning compression region 30*a*, in which the compression pressure at the first end is different than the compression pressure at the second end. As shown in FIG. 1 and according to certain embodiments, for example, the compression article 10 may comprise at least three uniform compression regions 20*a*, 20*b*, 20*c* and at least two transitioning compression regions (three in FIG. 1) 30*a*, 30*b*, 30*c*.

As shown in FIG. 1 and in accordance with certain embodiments, for instance, the compression article 10 may comprise a compression stocking. In such embodiments, for example, the compression article 10 may comprise at least an ankle portion and a calf portion with the ankle portion and the calf portion collectively comprising at least two compression regions capable of exerting a compression pressure on the body when the compression article is worn. For instance, in such embodiments, within each compression region, the compression pressure may be maximum proximate the ankle portion and/or proximate a region closest to the ankle portion. In other embodiments, for example, the compression article may further comprise a foot portion. According to certain embodiments, for instance, each of the ankle portion, calf portion, and/or foot portion may provide no compression pressure, uniform compression pressure, or graduated compression pressure.

According to certain embodiments, for instance, the first uniform compression region and the second uniform compression region may comprise different elastomeric yarns in order to provide different compression pressures along the compression article. The elastomeric yarn for each uniform compression region may be selected based on strain stretch properties, modulus, yarn count (e.g., denier), and/or the like. Elastomeric yarns, for instance, may generally resume an original shape (e.g., non-stretched or relaxed state) when a deforming force is removed. In certain embodiments, for instance, the elastomeric yarns may comprise from about 20 denier to about 150 denier. In other embodiments, for example, the elastomeric yarns may comprise from about 30 denier to about 120 denier. In further embodiments, for instance, the elastomeric yarns may comprise from about 50 denier to about 100 denier. As such, in certain embodiments, the elastomeric yarns may comprise from at least about any of the following: 20, 25, 30, 35, 40, 45, and 50 denier and/or at most about 150, 145, 140, 135, 130, 125, 120, 115, 110, 105 and 100 denier (e.g., about 35-130 denier, about 20-110 denier, etc.). By way of example only, the first uniform compression region may comprise a coarse count elastomeric yarn having higher modulus and more tension than the elastomeric yarn utilized in the second uniform compression region. In this regard, for instance, a different type of elastomeric yarn may be used in each uniform compression region, or the same type of elastomeric yarn may be used in each uniform compression region but with the elastomeric yarns used in each uniform compression region having different sizes (i.e. coarse or fine).

For example, in some embodiments, the elastomeric yarns may comprise spandex (i.e. Lycra®, elastane, etc.). In certain embodiments, for instance, the compression article may comprise at least 25 wt. % spandex. For example, in some embodiments, the compression article or certain regions of the compression article may comprise from about 25 wt. % to about 90 wt. % spandex. In other embodiments, for instance, the compression article or certain regions of the compression article may comprise from about 30 wt. % to about 80 wt. % spandex. In further embodiments, for example, the compression article or certain regions of the compression article may comprise from about 40 wt. % to about 60 wt. % spandex. As such, in certain embodiments, the compression article or certain regions of the compression article may comprise a weight percentage of spandex from at least about any of the following: 25, 30, 35, and 40 wt. % and/or at most about 90, 85, 80, 75, 70, 65, and 60 wt. % (e.g., about 30-80 wt. %, about 25-60 wt. %, etc.). In this regard, the different regions (e.g., uniform compression regions and transitioning compression regions) of a compression article may comprise different weight percentages of spandex or similar material, as described herein, within the foregoing ranges described above.

Figure 2:
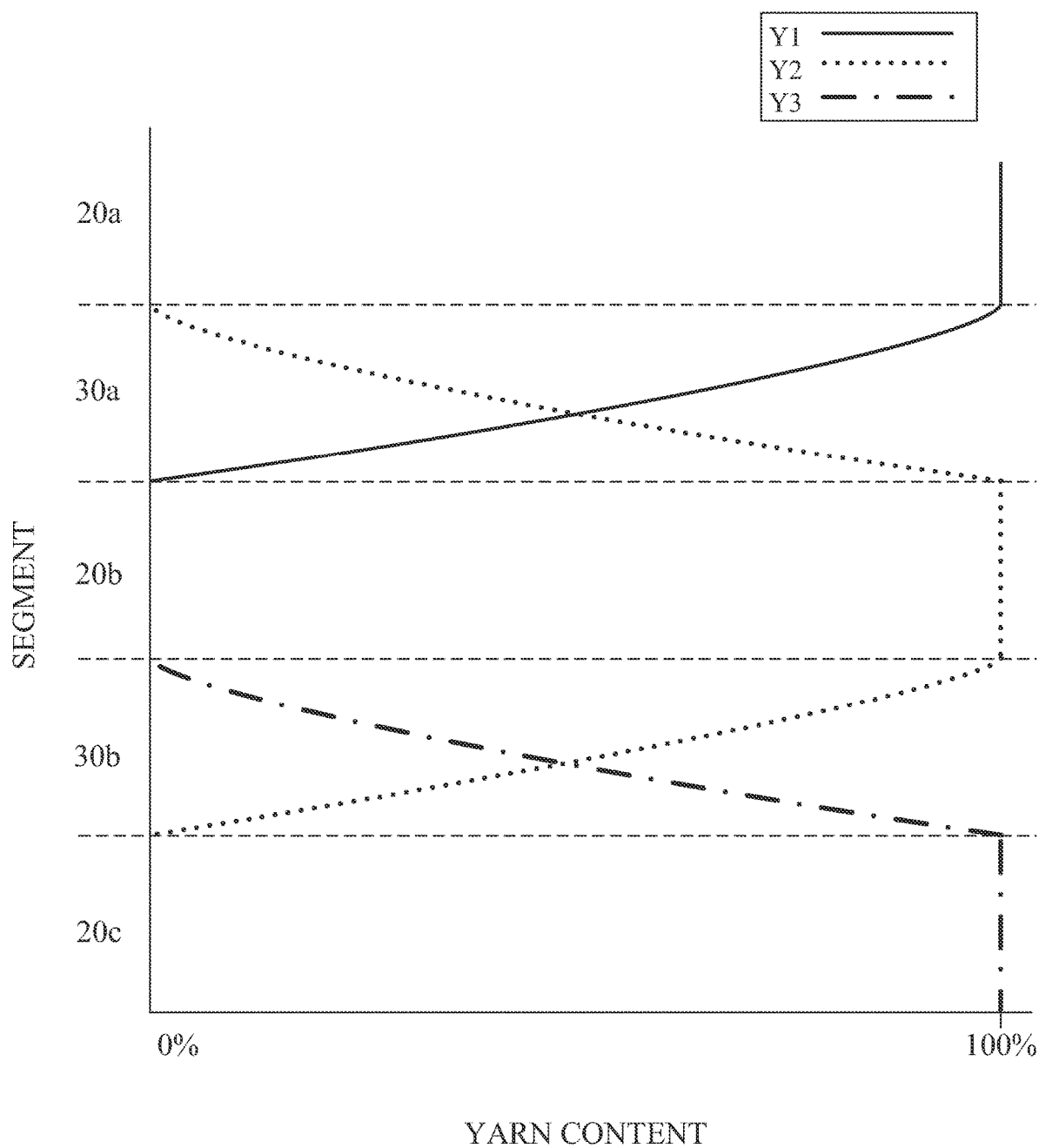
FIG. 2 illustrates a plot of yarn content by segments of an example embodiment illustrated in FIG. 1.

In certain embodiments, for example, the first uniform compression region may comprise at least predominantly a first yarn, the second uniform compression region may comprise a second yarn, and the first transitioning region may comprise a blend of at least the first yarn and the second yarn to define the compression pressure gradient. In this regard, for instance, in some embodiments, the first end of the first transitioning compression region may comprise a greater amount of the first yarn than the second yarn, and the second end of the first transitioning compression region may comprise a greater amount of the second yarn than the first yarn along the length of the first transitioning compression region. By varying the respective yarn concentrations along the length of the transitioning compression regions, for example, the transitioning compression regions may comprises a tailored compression pressure gradient or gradients along the length of the transitioning compression regions to minimize or eliminate unwanted abrupt changes in compression pressure along the length of the compression article. For example, FIG. 2 illustrates a simplified and exemplary change in yarn content across the respective regions of a compression article for the example embodiment illustrated in FIG. 1. That is, the illustration in FIG. 2 exemplifies just one approach according to an example embodiment and should not be construed as limiting. As shown in FIG. 2, the first uniform compression region 20*a* comprises by way of example and only for illustrative purposes 100% of yarn 1. Next, the first transitioning compression region 30*a* comprises by way of example and only for illustrative purposes a mixture of yarn 1 and yarn 2. As illustrated in FIG. 2, the mixture of the respective yarn content can be varied throughout the length of transitioning compression regions to provide, for example, localized compression pressure gradients throughout the length of the transitioning compression regions. For example, localized compression pressure gradients adjacent or proximate to an interface between the transitioning compression regions and one or more uniform compression regions may comprise a smaller magnitude then localized compression pressure gradients located near or in the middle of the transitioning compression regions to further buffer or minimize any abrupt changes in compression pressure across the various regions of the compression article. In this regard, the change in the mixture of blend of the fibers located in the transitioning compression regions need not be linear, and in accordance with certain embodiments is non-linear. As also illustrated in FIG. 2, the second uniform compression region 20*b* comprises by way of example and only for illustrative purposes 100% yarn 2. Next, the second transitioning compression region 30*b* comprises by way of example and only for illustrative purposes a mixture of yarn 2 and yarn 3. Finally, third uniform compression region comprises by way of example and only for illustrative purposes 100% yarn 3. FIG. 2 illustrates, for example, the configuration of a compression article comprising a plurality of different yarns, each having a respective elasticity, as well as blends of the different yarns forming different regions of the compression article to provide a tailored compression pressure profile along the length of the compression article. Such embodiments, for example, may be configured such that minimal compression pressure is realized at one or both ends of the compression article to allow for ease of application of the compression article, while simultaneously providing the desired level of compression pressure at the desired location(s) of the compression article.

In accordance with certain embodiments, for instance, the each of the uniform compression regions may comprise a compression pressure (e.g., the first compression pressure) independently selected from about 5 mmHg to about 40 mmHg. In other embodiments, for example, each of the uniform compression regions may comprise a compression pressure (e.g., the first compression pressure) independently selected from about 5 mmHg to about 24 mmHg (i.e. capillary pressure). In further embodiments, for instance, each of the uniform compression regions may comprise a compression pressure (e.g., the first compression pressure) independently selected from about 5 mmHg to about 15 mmHg. As such, in certain embodiments, each of the uniform compression regions may comprise a compression pressure (e.g., the first compression pressure) independently selected from at least about any of the following: 5, 10, 15, 20, and 24 mmHg and/or at most about 40, 35, 30, 24, 20, and 15 mmHg (e.g., about 10-40 mmHg, about 24-30 mmHg, etc.). For example, according to certain embodiments, for example, the first and second compression pressures may comprise from about 5 mmHg to about 40 mmHg. In other embodiments, for example, the first and second compression pressures may comprise from about 5 mmHg to about 24 mmHg. In further embodiments, for instance, the first and second compression pressures may comprise from about 5 mmHg to about 15 mmHg. As such, in certain embodiments, the first and second compression pressures may comprise from at least about any of the following: 5, 10, 15, 20, and 24 mmHg and/or at most about 40, 35, 30, 24, 20, and 15 mmHg (e.g., about 10-40 mmHg, about 24-30 mmHg, etc.). In accordance with certain embodiments, the first compression pressure is different than the second compression pressure. Each of the transitioning compression regions that may be located between a pair of uniform compression regions may comprise a compression pressure gradient or a plurality of localized compression pressure gradients confined within the foregoing pressure ranges. By way of an example for illustrative purposes, one embodiment may comprise a first uniform compression region comprising a compression pressure of, for example, about 20 mmHG and a second uniform compression region comprising a compression pressure of, for example, about 30 mmHG. In such an example embodiment, a first transitioning compression region may be located directly between and directly interface with both the first uniform compression region and the second uniform compression region. The first transitioning compression region, for example, may comprise a variable compression pressure along the length of the first transitioning compression region, in which the end of the first transitioning region adjacent or proximate to the first uniform compression region comprises a compression pressure slightly greater than 20 mmHH (e.g, 20.5 mmHG, 21 mmHG, 21.5 mmHG, 22 mmHG, etc. . . . ) and the other end of the first transitioning region adjacent or proximate to the second uniform compression region comprises a compression pressure slightly less than 30 mmHH (e.g, 29.5 mmHG, 29 mmHG, 28.5 mmHG, 28 mmHG, etc. . . . ). In accordance with such embodiments, for example, the compression pressures associated with transitioning compression regions located between uniform compression regions may not exceed the largest compression pressure associated with either of the adjacent uniform compression regions.

In some embodiments, for example, the first compression pressure may be greater than the second compression pressure. In this regard, for instance, the first uniform compression region may have a greater compression pressure than the second uniform compression region. In embodiments having more than two uniform compression regions, for example, the compression pressure of each uniform compression region may decrease as follows: first compression pressure >second compression pressure >third compression pressure, etc., or vice versa.

Figure 7:
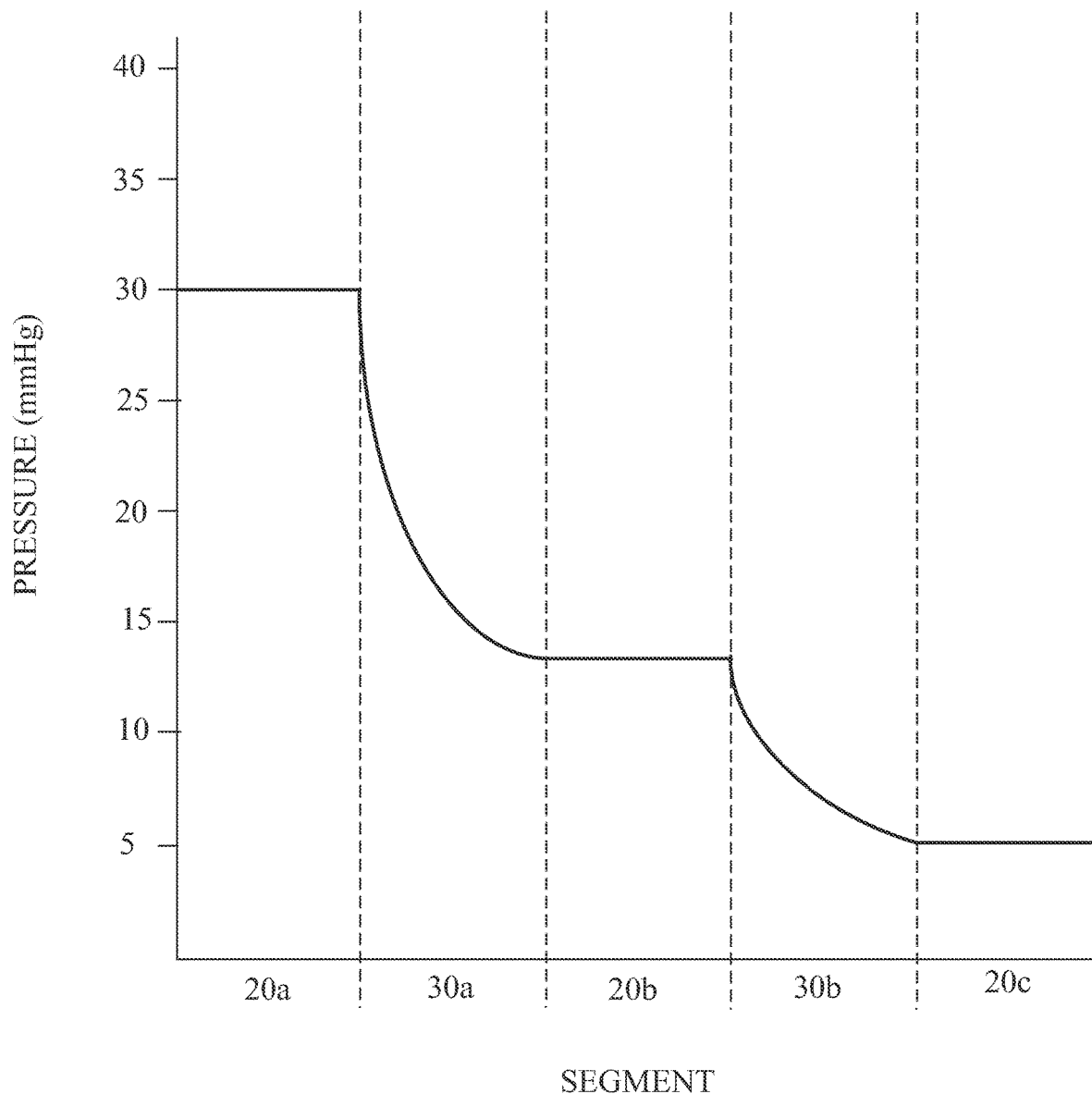
FIG. 7 illustrates a plot of pressure changes by segments of an example embodiment illustrated in FIG. 1.

In certain embodiments, for instance, the compression pressure gradient or any localized compression pressure gradient may comprise a compression pressure change from about 1% per inch to about 20% per inch. In other embodiments, for example, the compression pressure gradient or any localized compression pressure gradient may comprise a compression pressure change from about 1% per inch to about 10% per inch. In further embodiments, for instance, the compression pressure gradient a compression pressure change may comprise a compression pressure change from about 5% per inch to about 10% per inch. As such, in certain embodiments, the compression pressure gradient or any localized compression pressure gradient may comprise a compression pressure change from at least about any of the following: 1, 2, 3, 4, and 5% per inch and/or at most about 20, 18, 16, 14, 12, and 10% per inch (e.g., about 3-18% per inch, about 1-10% per inch, etc.). For example, FIG. 7 illustrates an exemplary plot of compression pressure changes by segments of an example embodiment illustrated in FIG. 1. As shown in FIG. 7, the first uniform compression region 20a provides a uniform compression pressure, which decreases at a variable rate (although the pressure change could be linear if desired) through the first transitioning compression region 30a. Next, the second uniform compression region 20b provides a uniform compression pressure lower than that of the first uniform compression region 20a. The second uniform compression pressure decreases at a variable rate (although the pressure change could be linear if desired) through the second transitioning compression region 30b and stabilizes to the lowest uniform compression pressure in the third uniform compression region 20c. As illustrated in FIG. 7, the compression pressure changes along the length of the transitioning compression regions may not be uniform or linear along the length of the transitioning compression regions. For instance, the overall compression pressure gradient for each transitioning compression region may comprise or be defined by a plurality of localized compression pressure gradients that vary in magnitude to provide a tailored or custom pressure profile along that particular segment or region of the compression article. For instance, one or more of the transitioning compression regions may comprise a first localized compression pressure gradient adjacent or proximate an interface between the transitioning compression region and a uniform compression region that is smaller in magnitude than a second localized compression pressure gradient located at or proximate the middle of the transitioning compression region. Similarly, one or more of the transitioning compression regions may also comprise a third localized compression pressure gradient adjacent or proximate an interface between the transitioning compression region and a second (and different) uniform compression region that is smaller in magnitude than the second localized compression pressure gradient located at or proximate the middle of the transitioning compression region. Such embodiments, for instance, may provide a smooth compression pressure transition from the uniform compression regions into and through the transitioning compression regions.

Moreover, the compression pressure gradient may be defined and/or impacted by an angle of compression that is created by changes in graded compression pressures that arise due to changes in the general shape of muscles of a wearer. By way of example only, compression stockings according to certain embodiments, for instance, may utilize graded compression pressures as discussed above (e.g., localized compression pressure gradients) that change as the compression stocking extends from the ankle toward the calf regions due to changes, for instance, in the general shape of leg muscles. The angle of compression for a segment within a compression article may be defined as follows by Equation 1:

$$ac = -(c_2 - c_1)d \qquad (1)$$

wherein ac is the angle of compression, $c_1$ is the compression at a first edge of a segment or a portion of the segment, $c_2$ is the compression at the second edge of the segment or a portion of the segment, and d is the distance between the points where the compression measurements were taken. Equation 1 includes a negative sign to convert the negative slope to a positive number. A segment having an angle of compression equal to zero (i.e. $c_1 = c_2$) is a segment having uniform compression (e.g., the first uniform compression region, the second uniform compression region, etc.).

In accordance with certain embodiments, for instance, each transitioning compression region (e.g., the first transitioning compression region) may comprise from about 1% to about 50% of an unstretched length of the compression article. In other embodiments, for example, each transitioning compression region (e.g., the first transitioning compression region) may comprise from about 5% to about 40% of an unstretched length of the compression article. In further embodiments, for instance, each transitioning compression region (e.g., the first transitioning compression region) may comprise from about 10% to about 30% of an unstretched length of the compression article. As such, in certain embodiments, each transitioning compression region (e.g., the first transitioning compression region) may comprise an unstretched length of the compression article from at least about any of the following: 1, 3, 5, 8, and 10% and/or at most about 50, 45, 40, 35, and 30% (e.g., about 3-40%, about 10-50%, etc.). Similarly, in some embodiments, for example, the first uniform compression region and the second uniform compression region may comprise from about 50% to about 99% of the unstretched length of the compression article. In other embodiments, for instance, the first uniform compression region and the second uniform compression region may comprise from about 60% to about 95% of the unstretched length of the compression article. In further embodiments, for example, the first uniform compression region and the second uniform compression region may comprise from about 70% to about 90% of the unstretched length of the compression article. As such, in certain embodiments, the first uniform compression region and the second uniform compression region may comprise an unstretched length of the compression article from at least about any of the following: 50, 55, 60, 65, and 70% and/or at most about 99, 97, 95, 93, and 90% (e.g., about 55-93%, about 50-90%, etc.).

Figure 3A:
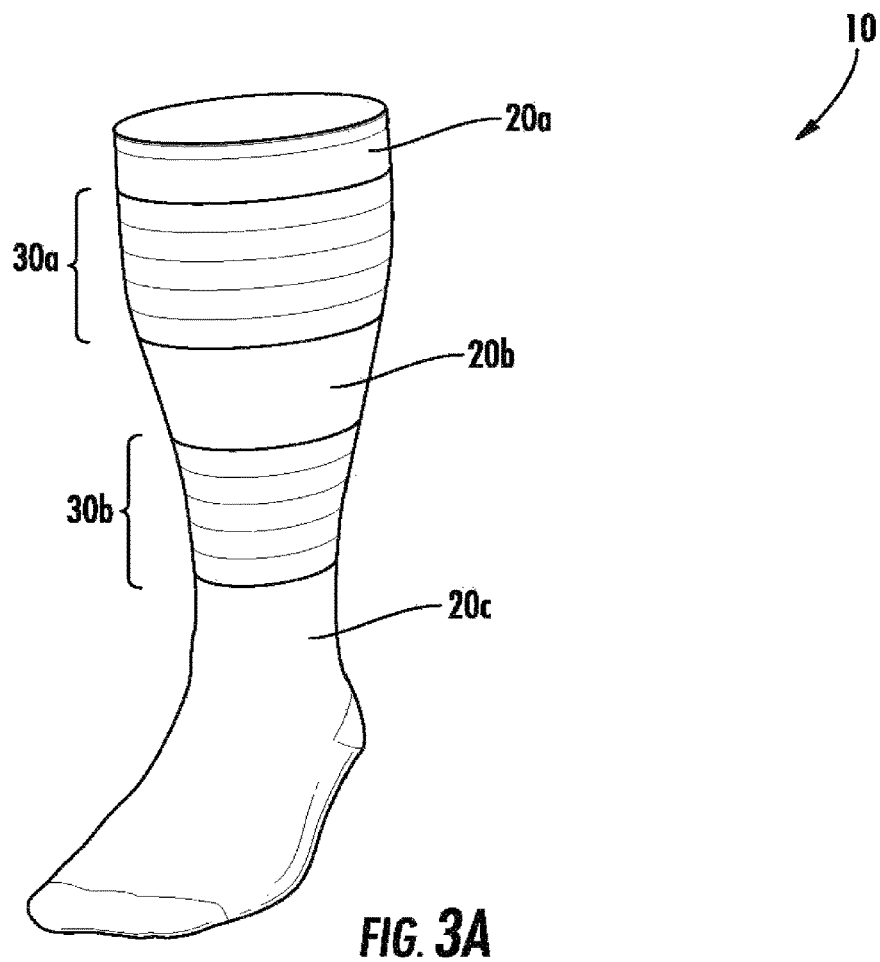
FIGS. 3A-3G illustrate various banded compression articles in accordance with example embodiments.

According to certain embodiments, for instance, each transitioning compression region (e.g., the first transitioning compression region) may comprise an unstretched length from about 0.1 cm to about 50 cm. In other embodiments, for example, each transitioning compression region (e.g., the first transitioning compression region) may comprise an unstretched length from about 0.1 cm to about 45 cm. In further embodiments, for instance, each transitioning compression region (e.g., the first transitioning compression region) may comprise an unstretched length from about 5 cm to about 25 cm. As such, in certain embodiments, each transitioning compression region (e.g., the first transitioning compression region) may comprise an unstretched length from at least about any of the following: 0.1, 0.5, 1, 2, 3, 4, and 5 cm and/or at most about 50, 48, 45, 30, 35, and 25 cm (e.g., about 0.5-48 cm, about 0.1-30 cm, etc.). Moreover, according to certain embodiments and as illustrated in FIG. 1, for example, at least one of the first uniform compression region 20a and the second uniform compression region 20b may have an unstretched length that is greater than an unstretched length of the first transitioning compression region 30a. However, in other embodiments and as illustrated in FIG. 3A, for instance, at least one of the first uniform compression region 20a and the second uniform compression region 20b may have an unstretched length that is less than an unstretched length of the first transitioning compression region 30a.

Figure 3B:
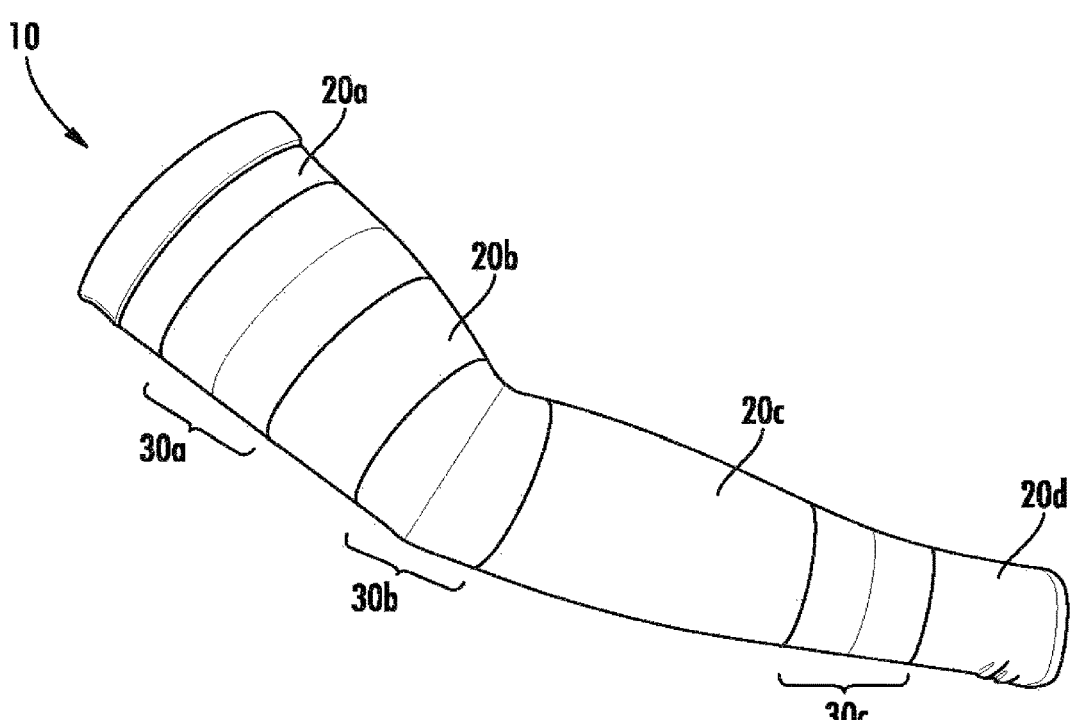
Figure 3C:
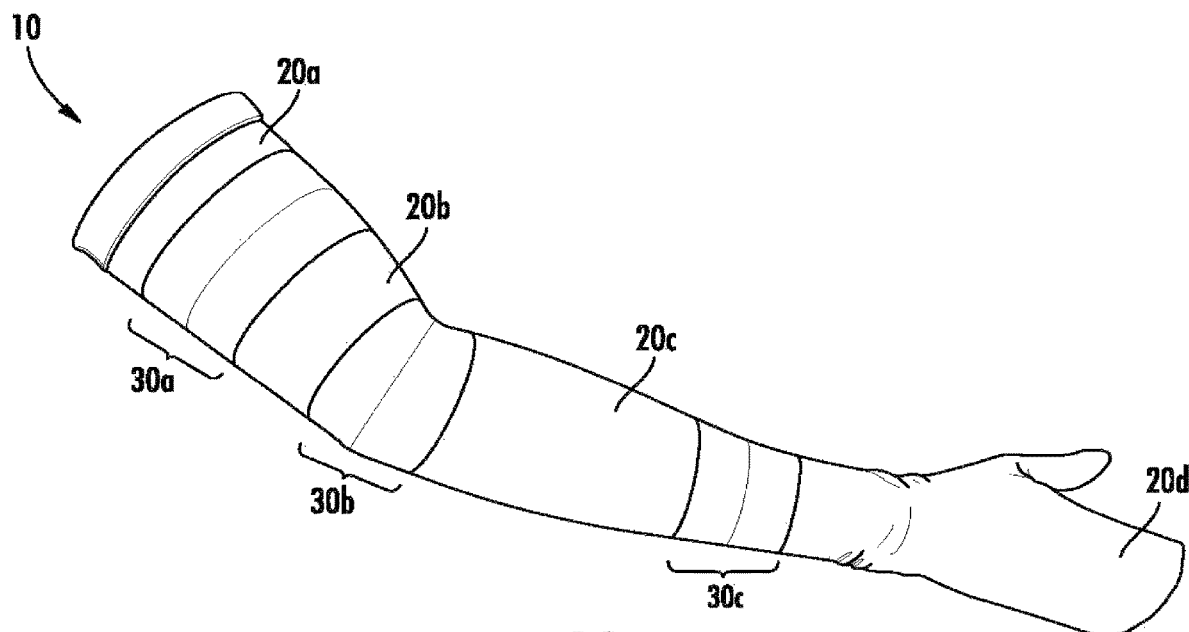
Figure 3D:
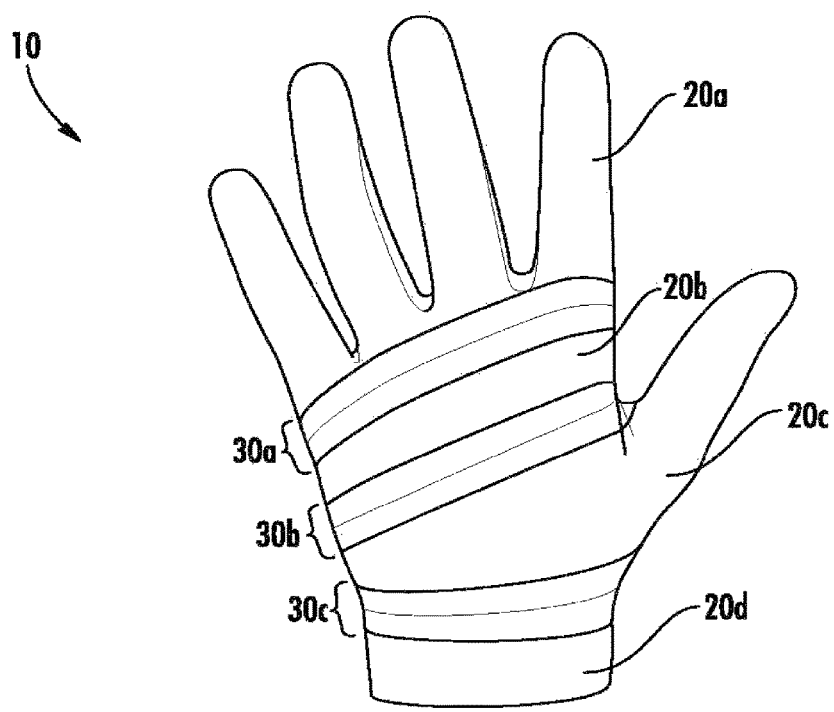
Figure 3E:
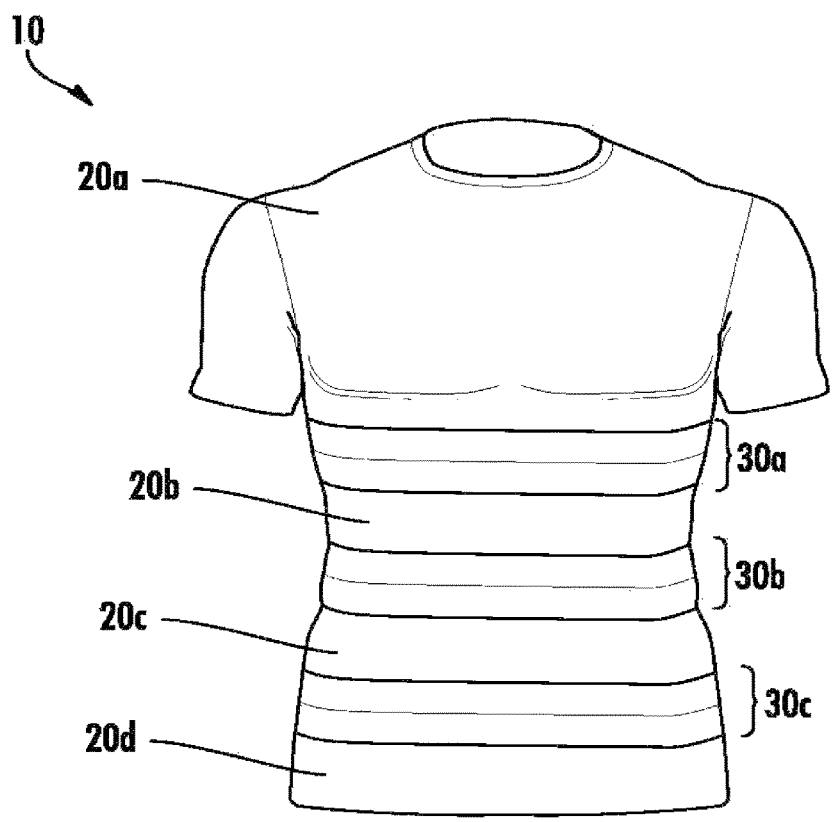
Figure 3F:
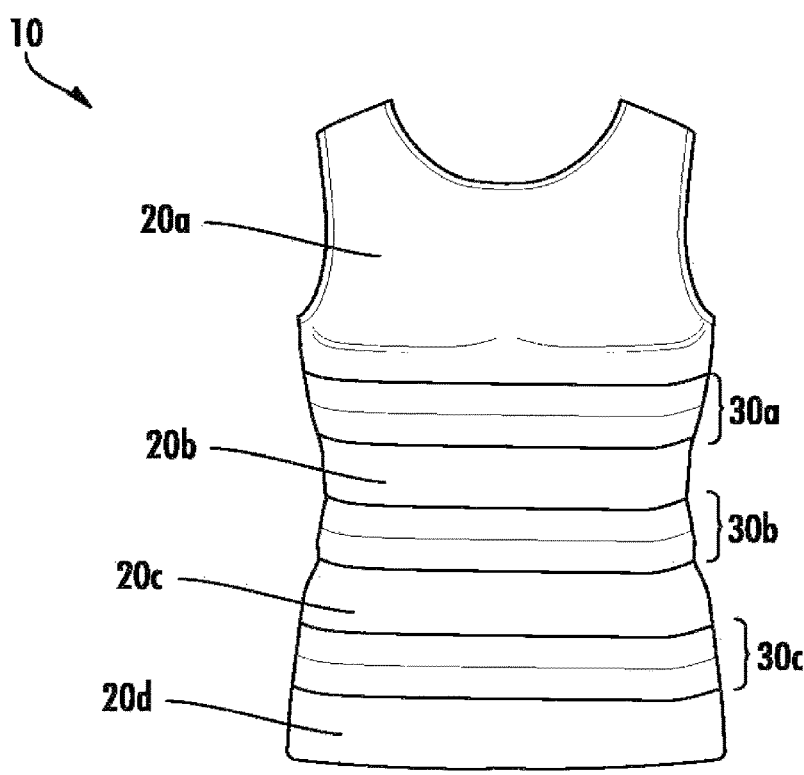
Figure 3G:
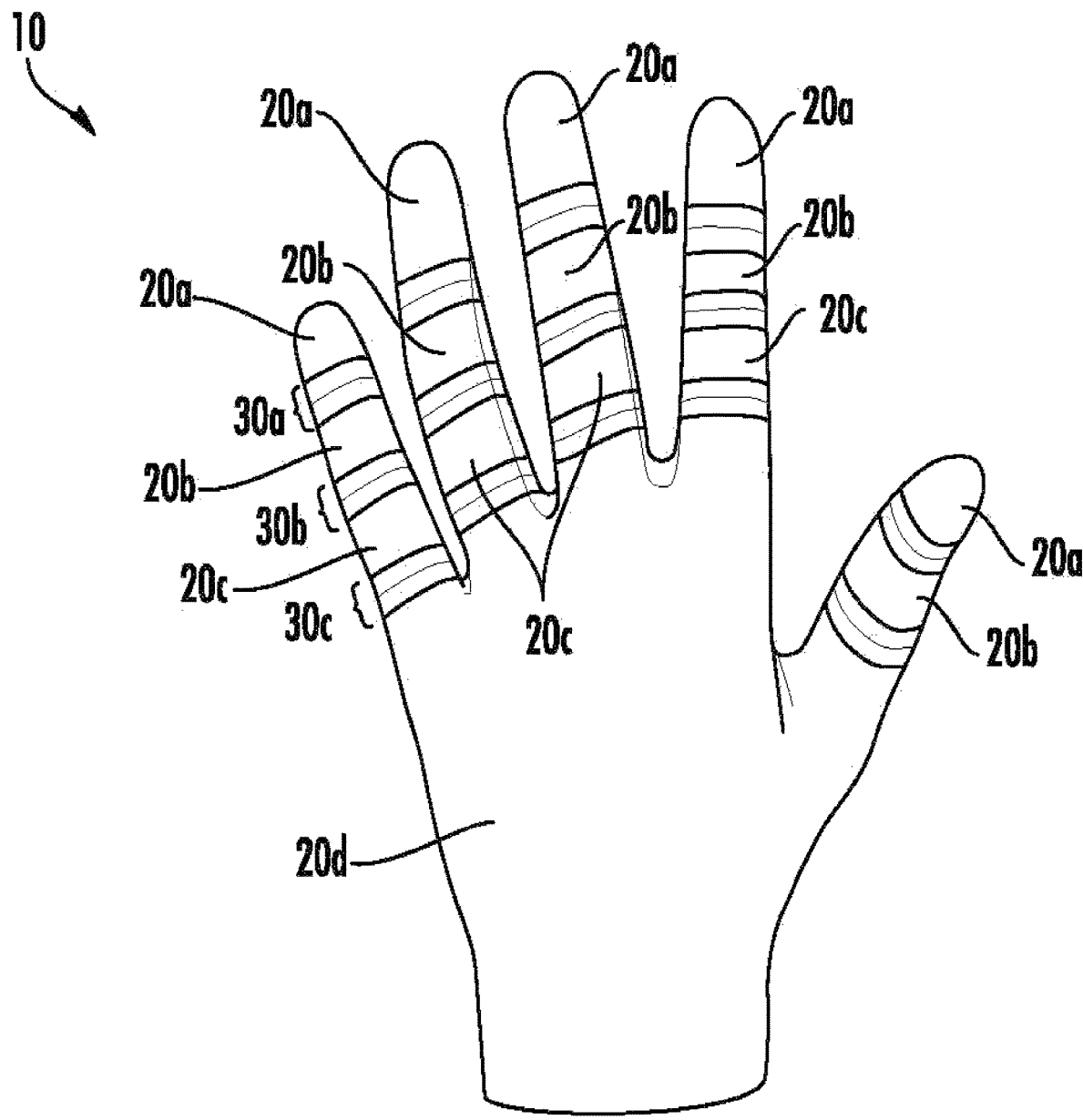

According to certain embodiments, for example, the first uniform compression region, the second uniform compression region, and the first transitioning compression region may extend around or define a circumference of the compression article. For example, FIGS. 3A-3G illustrate various banded compression articles in accordance with example embodiments. For instance, in some embodiments and as shown in FIG. 3A, the compression article 10 may comprise a compression stocking. Moreover, in other embodiments and as shown in FIG. 3B, for example, the compression article 10 may comprise a handless compression sleeve. In further embodiments and as shown in FIG. 3C, for instance, the compression article 10 may comprise a compression sleeve having a hand portion. In other embodiments and as shown in FIG. 3D, for example, the compression article 10 may comprise a compression glove having compression regions 20a-20c, 30a-30c on the hand portion of the compression glove. In further embodiments and as shown in FIG. 3E, for instance, the compression article 10 may comprise a compression shirt. In some embodiments and as shown in FIG. 3F, the compression article 10 may comprise a compression vest. In other embodiments and as shown in FIG. 3G, the compression article 10 may comprise a compression glove having compression regions 20a-20c, 30a-30c on the finger portions of the compression glove.

In accordance with certain embodiments, for example, the first uniform compression region, the second uniform compression region, and the first transitioning compression region may extend across a weft width direction of the compression article. In such embodiments, for example, the compression article may exert radial compression across the weft width direction. According to certain embodiments, for instance, each uniform compression region may gradually interact with another uniform compression region. In this regard, for example, the uniform compression regions may define transitioning compression regions that comprise portions of both uniform compression regions opposed adjacently to the transitioning compression region. As such, the uniform compression regions may exert radial compression, while the transitioning compression regions may exert gradual compression. FIGS. 4A-4F illustrate such example embodiments and may be formed via a seamless knitting machine using automatic knitter/knotter of the elastomeric yarns moving from section to the other. The elastomeric yarn of each uniform compression region may have at least one of a different modulus, different size, different stress-strain curve, and/or any combination thereof from other elastomeric yarns utilized in other uniform compression regions.

Figure 4A:
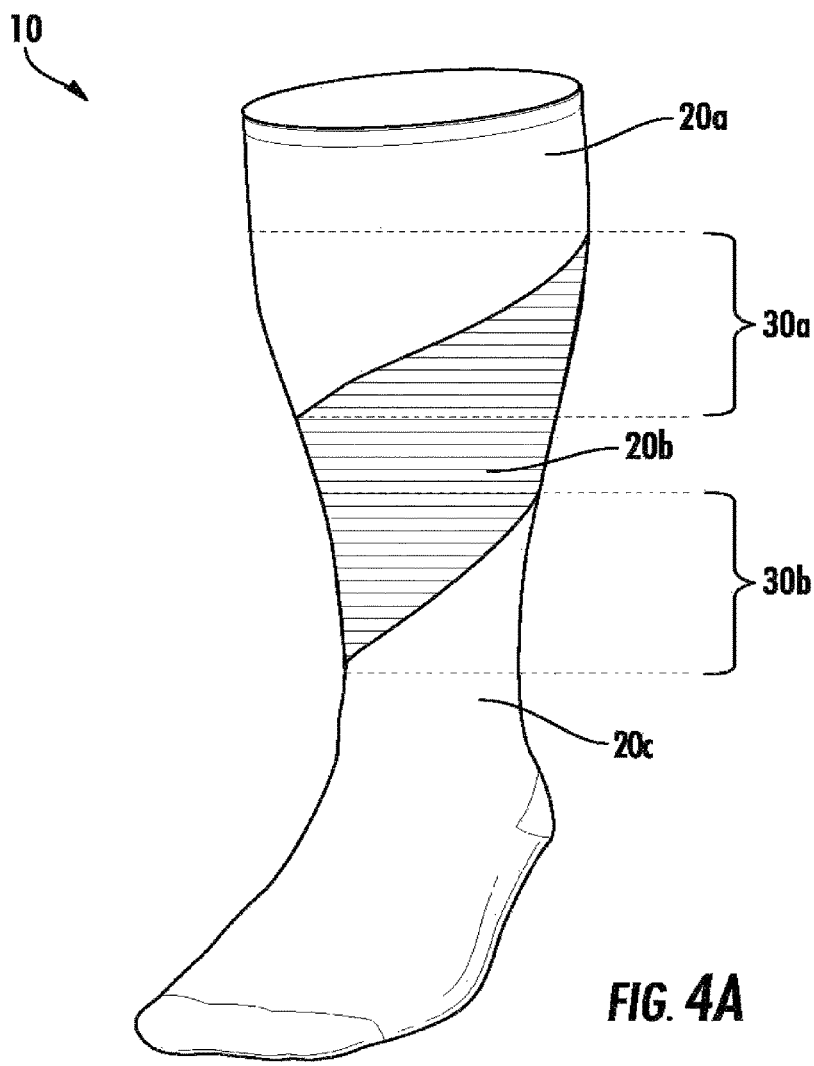
FIGS. 4A-4F illustrate various radial compression articles in accordance with example embodiments.
Figure 4B:
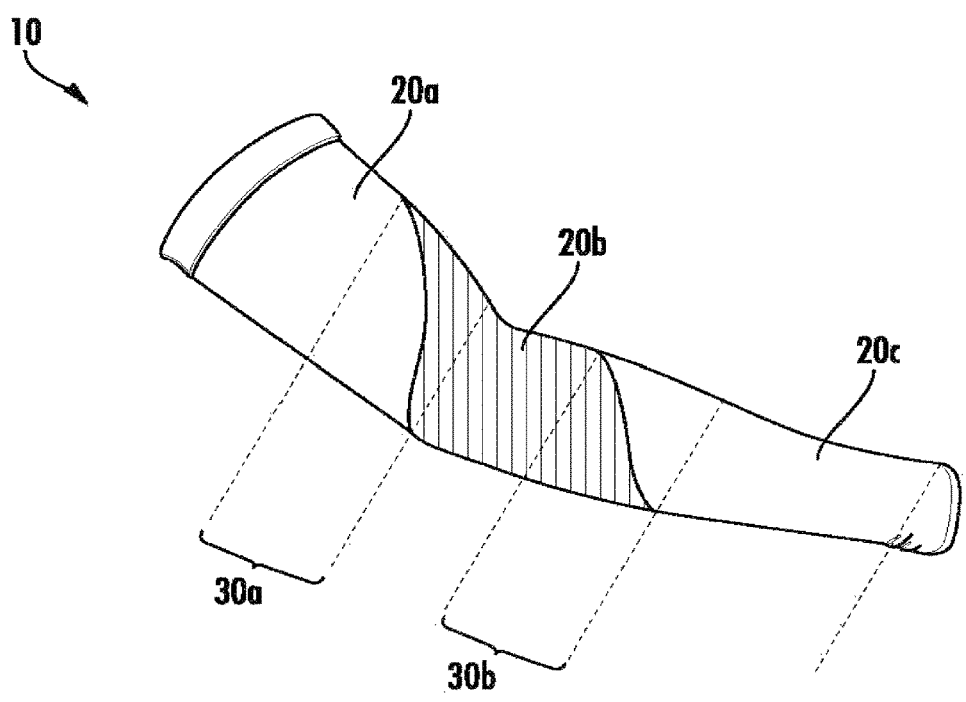
Figure 4C:
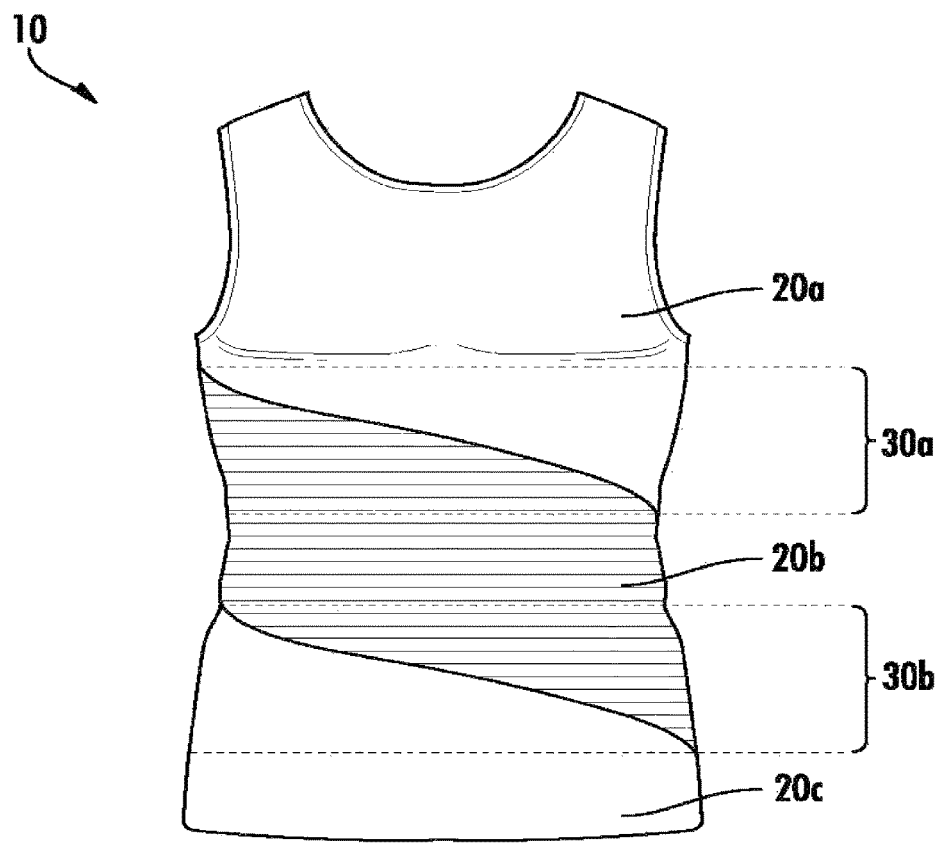
Figure 4D:
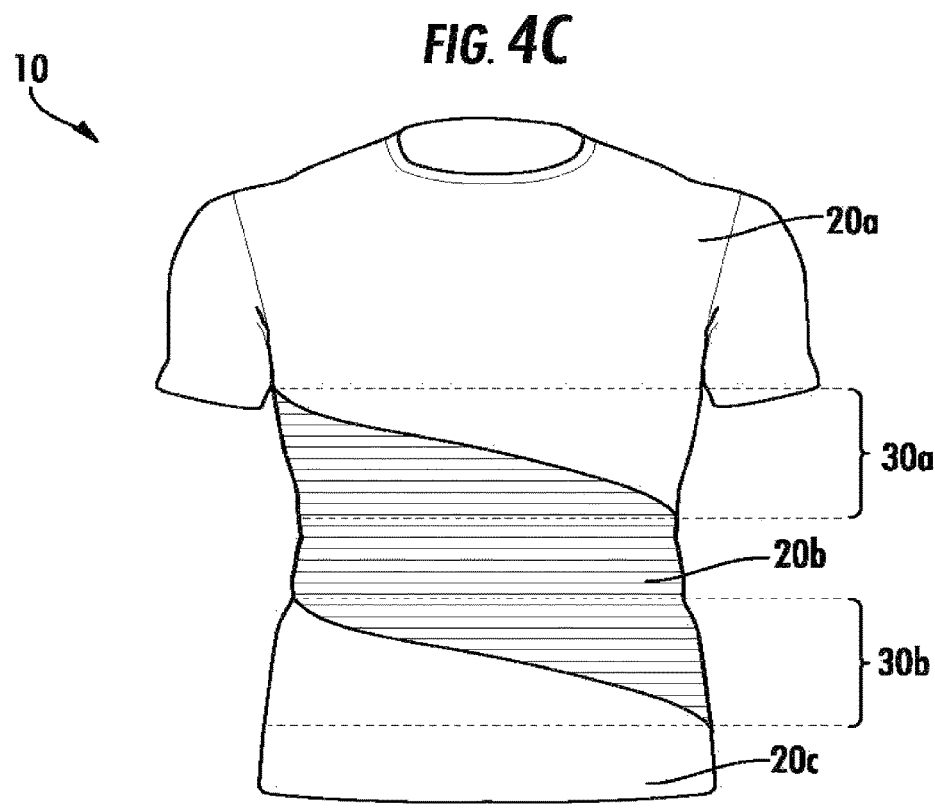
Figure 4E:
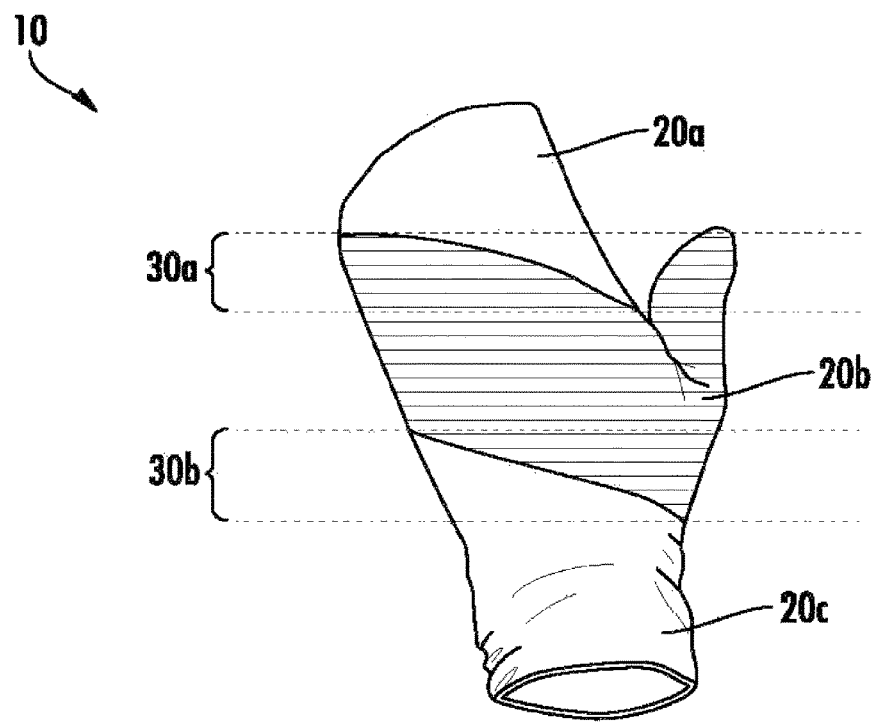
Figure 4F:
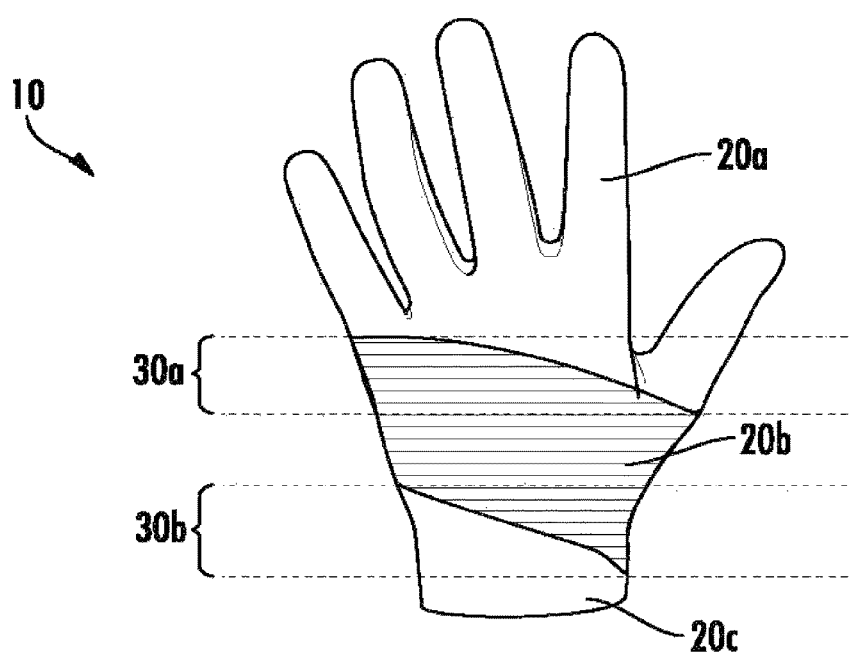

For example, FIGS. 4A-4F illustrate various radial compression articles in accordance with certain example embodiments. For instance, in some embodiments and as shown in FIG. 4A, the compression article 10 may comprise a compression stocking. Moreover, in other embodiments and as shown in FIG. 4B, for example, the compression article 10 may comprise a handless compression sleeve. In further embodiments and as shown in FIG. 4C, for instance, the compression article 10 may comprise a compression vest. In other embodiments and as shown in FIG. 4D, for example, the compression article 10 may comprise a compression shirt. In further embodiments and as shown in FIG. 4E, for instance, the compression article 10 may comprise a compression mitt. In some embodiments and as shown in FIG. 4F, the compression article 10 may comprise a compression glove.

Figure 6A:
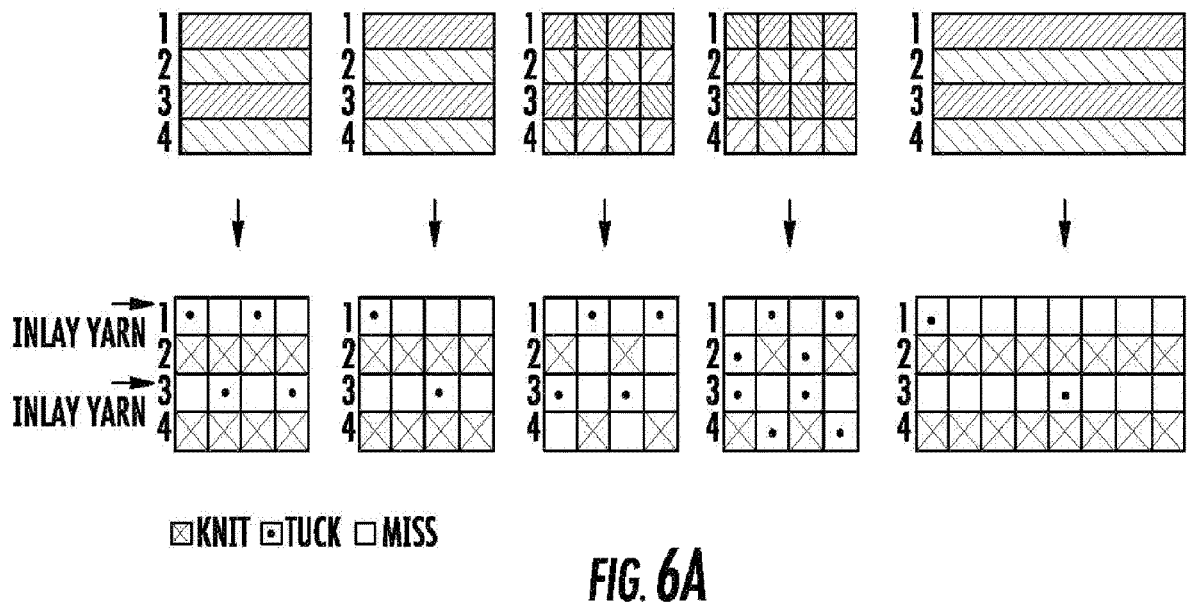
FIGS. 6A-6B illustrate stitch diagrams for compression article fabric having an elastic component and a relaxed component in accordance with example embodiments.
Figure 6B:
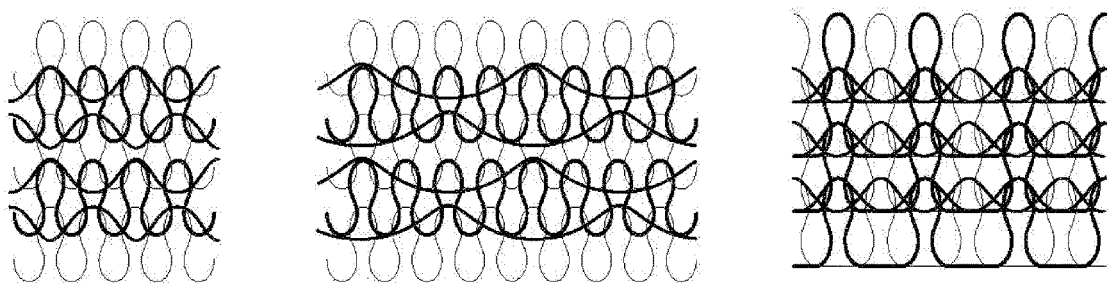
Figure 6B:
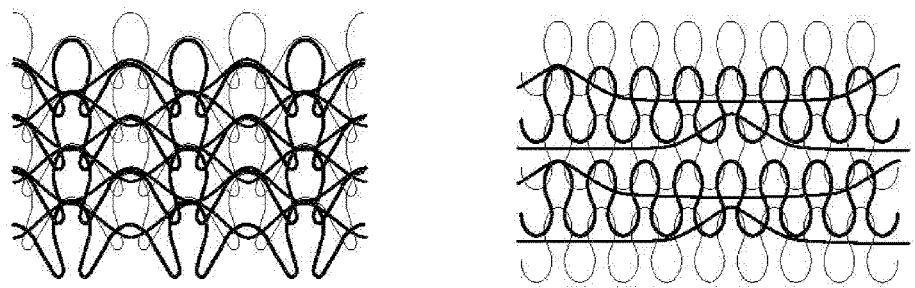

In accordance with certain embodiments, for instance, the compression article may comprise a material having an elastic component and a relaxed component. In this regard, for example, the elastic component and the relaxed component may be incorporated in a manner to provide uniform compression pressure, graduated compression pressure (e.g., compression pressure gradients), and/or a combination thereof within the compression article. For example, more than one elastomeric yarn feed may be used in the same lay-in position, and one feed may provide the elastic component while the other feed may provide the relaxed component in a predetermined pattern and/or design, as shown in the exemplary stitch diagrams for compression article fabric illustrated in FIGS. 6A and 6B. That is, the stitch diagrams illustrated in FIGS. 6A and 6B are merely exemplary in nature and are not limiting. As such, when the compression article is not being worn, the elastic component may remain in an un-stretched state, but when placed on a wearer, the elastic component may stretch in order to provide a desired level of compression. Moreover, in some embodiments, for instance, the elastic component may target compression on specific muscle groups. The level of compression pressure provided by the compression article may be governed by the size of the article along with the amount of fabric stretching, as dictated by Laplace's law, which indicates that the larger the vessel radius, the larger the wall tension required to withstand a given internal fluid pressure. Similarly, when the compression article is not being worn, for example, the relaxed component may be in a gathered state, but when placed on a wearer, the relaxed component expands without applying compression. In this regard, for instance, substantially all of the compression pressure generated by the compression article may be derived from the stretch of the elastic component.

Figure 5:
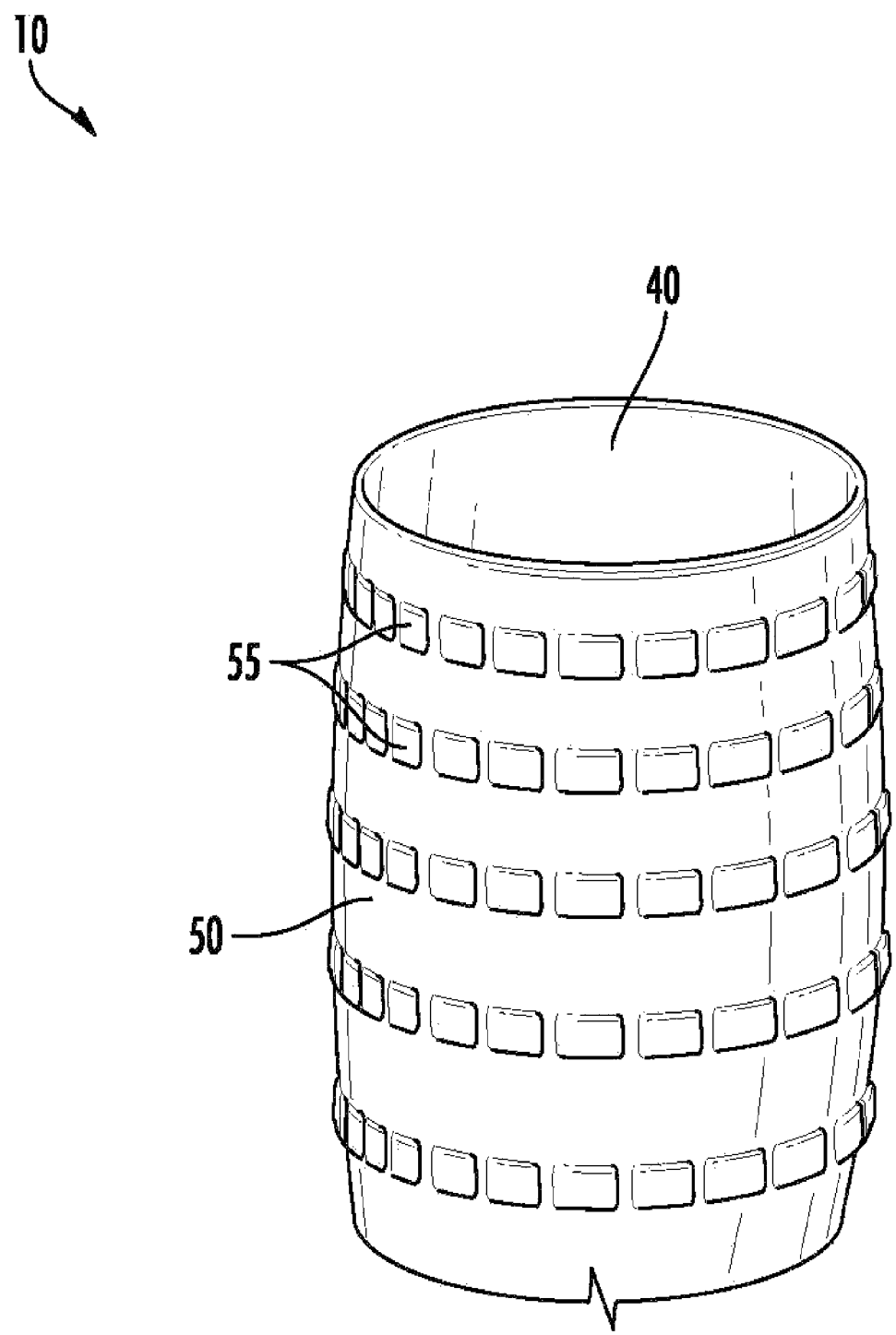
FIG. 5 illustrates the surface textures of a compression article according to an example embodiment.

Moreover, according to certain embodiments, for example, an outer surface of the compression article may comprise raised wales, and a skin surface of the compression article may comprise a smooth surface. For example, FIG. 5 illustrates the surface textures of a compression article according to an example embodiment. As shown in FIG. 5, the compression article 10 has a skin surface 40 and an outer surface 50. The skin surface 40 is smooth, but the outer surface 50 comprises a plurality of raised wales 55. In this regard, for instance, the smooth surface may reduce stress concentration on the skin upon compression and may also provide a comfortable, smooth surface to contact the skin. Similarly, in accordance with certain embodiments, for instance, the compression article may be seamless to further provide a comfortable, smooth surface to contact the skin. In addition, for example, the raised wales may aid in producing effective pressure because the wale direction aids in one dimensional fabric stretching.

According to certain embodiments, for example, the compression article may comprise a thickness (e.g., a z-direction) from about 0.1 mm to about 1.0 mm. In other embodiments, for instance, the compression article may comprise a thickness from about 0.25 mm to about 0.75 mm. In certain embodiments, for example, the compression article may comprise a thickness from about 0.4 mm to about 0.6 mm. In further embodiments, for example, the compression article may comprise a thickness of about 0.5 mm. As such, in certain embodiments, the compression article may comprise a thickness from at least about any of the following: 0.1, 0.15, 0.2, 0.25, 0.3, 0.35, 0.4, 0.45, and 0.5 mm and/or at most about 1.0, 0.95, 0.9, 0.85, 0.8, 0.75, 0.7, 0.65, 0.6, 0.55, and 0.5 mm (e.g., about 0.25-0.85 mm, about 0.5-0.75 mm, etc.). In addition, according to certain embodiments, for instance, the compression article may comprise an area density from about 100 gsm to about 350 gsm. In other embodiments, for example, the compression article may comprise an area density from about 100 gsm to about 320 gsm. In further embodiments, for instance, the compression article may comprise an area density from about 102 gsm to about 313 gsm. As such, in certain embodiments, the compression article may comprise an area density from at least about any of the following: 100, 101, and 102 gsm and/or at most about 350, 340, 330, 320, 318, 315, and 313 gsm (e.g., about 100-315 gsm, about 102-330 gsm, etc.).

Thus, the invention includes compression articles suitable for a wide variety of uses (e.g., compression socks, athletic garments, shapewear, etc.). In accordance with certain embodiments, the compression article may include at least two uniform compression regions, including a first uniform compression region having a first compression pressure and a second uniform compression region having a second compression pressure, and at least one transitioning compression region, including a first transitioning compression region positioned between the first and second uniform compression regions, in which the first transitioning compression region comprises a first end adjacent or proximate to the first uniform compression region and a second end adjacent or proximate to the second uniform compression region. The first transitioning compression region comprises a compression pressure gradient extending from the first end to the second end of the first transitioning compression region. The compression pressure gradient may comprise or be defined by a plurality of localized compression pressure gradients within the first transitioning compression region.

In another aspect, certain embodiments of the invention provide a method for making a seamless compression article. In accordance with certain embodiments, the method includes forming at least a first uniform compression region comprising a first uniform compression pressure and forming a first transitioning compression region adjacent or proximate to the first uniform compression region, in which the first transitioning compression region comprises a first end adjacent or proximate to the first uniform compression region and a second end opposite the first end. The method may also comprise forming a second uniform compression region adjacent or proximate to the second end of the first transitioning compression region, in which the second uniform compression region comprises a second compression pressure being different from the first compression pressure. In such embodiments, for instance, the first transitioning compression region may be located between the first uniform compression region and the second uniform compression region, and the first transitioning compression region may comprise a compression pressure gradient extending from the first end to the second end of the first transitioning compression region as described throughout the present disclosure.

Figure 8:
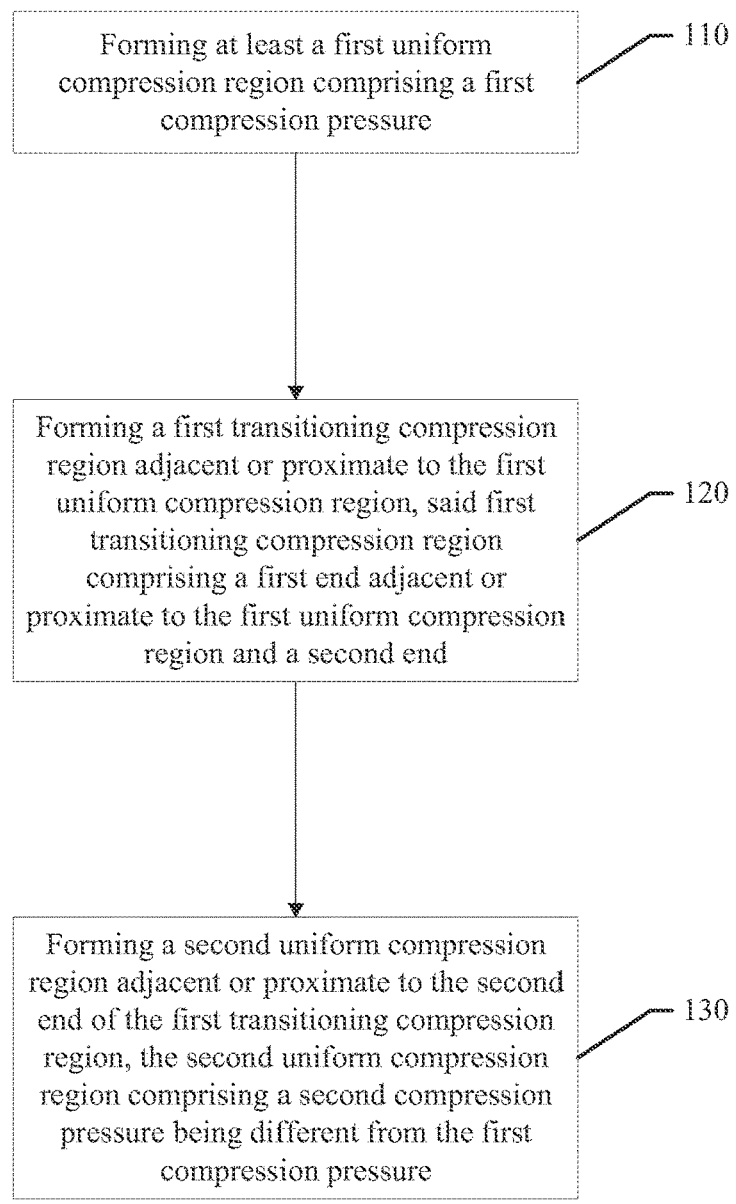
FIG. 8 illustrates a process flow diagram for making a seamless compression article according to an example embodiment.

FIG. 8, for example, illustrates a process flow diagram for making a seamless compression article according to an example embodiment. As shown in FIG. 8, the method may include forming at least a first uniform compression region comprising a first compression pressure at operation 110, forming a first transitioning compression region adjacent or proximate to the first uniform compression region, said first transitioning compression region comprising a first end adjacent or proximate to the first uniform compression region and a second end at operation 120, and forming a second uniform compression region adjacent or proximate to the second end of the first transitioning compression region, the second uniform compression region comprising a second compression pressure being different from the first compression pressure at operation 130.

In accordance with certain embodiments, for example, the uniform compression regions and the transitioning compression regions described above may comprise a laid-in stitch base fabric knit and an inlay yarn. In some embodiments, for instance, the laid-in fabric may comprise a ground structure knitted yarn held in position. As such, the laid-in fabric may provide thickness and stiffness to the compression article. In some embodiments, for example, the laid-in fabric may include, but is not limited to, synthetic fibers, natural fibers, and fibers derived from natural products. In certain embodiments, for instance, synthetic fibers may comprise (but are not limited to) nylon fibers, acrylic fibers, polyester fibers, and polypropylene fibers. In further embodiments, for example, yarns having a natural source may be obtained from cotton, wool, bamboo, hemp, alpaca and/or the like. In some embodiments, for instance, yarns derived from and/or manufactured from a natural source may be obtained from soy protein, corn, and the like. According to certain embodiments, for example, yarns having filament may have either a flat or textured form. Examples of such filament forms of yarn may include, but are not limited to, nylon, polyester, polypropylene and/or the like. The various yarns described herein, for instance, may be used individually or in combination with each other. Further, the yarn combinations may be formed, for example, in the knitting process or in a separate process prior to the knitting process. According to certain embodiments, for instance, the inlay yarn may include (but is not limited to) an elastomeric yarn comprising rubber, spandex or other elastic material such as Lycra® fiber. In some embodiments, for example, the spandex and/or rubber may be incorporated into the compression article by being laid-in, knit-in and/or the like. Moreover, in certain embodiments, for instance, the spandex and/or rubber may comprise bare spandex laid-in or plaited with the knit fabric. In further embodiments, for example, the spandex and/or rubber may be commingled with other fibers (e.g., nylon, polyester, polypropylene, etc.) to form a synthetic filament yarn. In other embodiments, for instance, the spandex and/or rubber may be covered by at least one of filament yarn, spun yarn (e.g., natural fibers like cotton, wool, etc. or a blend of natural fibers with synthetic fibers such as a polyester/cotton blend) and/or the like. In further embodiments, for instance, the elastomeric yarns may further comprise a covering of flat and/or textured filament yarns such as nylon, polyester or polypropylene.

In accordance with certain embodiments, for example, the inlay yarn may be incorporated into the laid-in fabric without knitting into loops during the same knitting cycle using the seamless knitting machine in order to generate the particular compression pressures generated by the compression article. To provide the compression pressure gradient or gradients, for example, a different elastomeric yarn, blend of yarns, and/or different sized yarns may be used as the inlay yarn in each uniform compression region. In such embodiments, for instance, each elastomeric yarn, for example, may be selected based on its tension, modulus, and/or yarn size. In other embodiments, for example, varying a mixture of yarns may provide an overall change in compression pressure. In this regard, for instance, the compression pressure may be varied among the uniform compression regions and the transitioning compression regions by varying yarn types or mixtures of yarn content based on the selection of yarns having a particular elasticity and/or modulus and/or by varying the respective yarn sizes of the individual compression regions.

Although exemplary knitting processes have been described herein, one of ordinary skill in the art should understand that this disclosure is not limited to such knitting processes. In fact, any knitting process suitable for producing the compression article described herein as understood by one of ordinary skill in the art may be used. Moreover, all disclosures regarding the compression article are hereby incorporated into the method disclosures discussed herein.

Non-Limiting Exemplary Embodiments

Having described various aspects and embodiments of the invention herein, further specific embodiments of the invention include those set forth in the following paragraphs.

Certain embodiments according to the invention provide compression articles suitable for a wide variety of uses (e.g., compression socks, athletic garments, shapewear, etc.). In accordance with certain embodiments, the compression article includes at least two (e.g., 2, 3, 4, 5, 6, 7, 8, etc.) uniform compression regions, including a first uniform compression region having a first compression pressure and a second uniform compression region having a second compression pressure, and at least one transitioning compression region, including a first transitioning compression region positioned between the first and second uniform compression regions The first transitioning compression region may comprise a first end adjacent or proximate to the first uniform compression region and a second end adjacent or proximate to the second uniform compression region. The first transitioning compression region may comprise a compression pressure gradient extending from the first end to the second end of the first transitioning compression region. In further embodiments, the compression article comprises at least three uniform compression regions and at least two transitioning compression regions.

In accordance with certain embodiments, the first compression pressure comprises from about 5 mmHg to about 40 mmHg. In some embodiments, the first compression pressure is greater than the second compression pressure. Moreover, in certain embodiments, the compression pressure gradient comprises a change in pressure of about 1% per inch to about 20% per inch.

According to certain embodiments, the first uniform compression region and the second uniform compression region comprise different elastomeric yarns. In some embodiments, the elastomeric yarns comprise spandex. In further embodiments, the elastomeric yarns comprise from about 20 denier to about 150 denier. In certain embodiments, the first uniform compression region comprises at least predominantly a first yarn, the second uniform compression region comprises a second yarn, and the first transitioning region comprises a blend of at least the first yarn and the second yarn to define the compression pressure gradient. In some embodiments, the first end of the first transitioning compression region comprises a greater amount of the first yarn than the second yarn, and the second end of the first transitioning compression region comprises a greater amount of the second yarn than the first yarn.

In accordance with certain embodiments, the first transitioning compression region comprises from about 1% to about 50% of an unstretched length of the compression article. In some embodiments, the first uniform compression region and the second uniform compression region comprise from about 50% to about 99% of the unstretched length of the compression article. In further embodiments, the first transitioning compression region comprises an unstretched length from about 0.1 cm to about 50 cm. Moreover, according to certain embodiments, at least one of the first uniform compression region and the second uniform compression region has an unstretched length that is greater than an unstretched length of the first transitioning compression region. In further embodiments, at least one of the first uniform compression region and the second uniform compression region has an unstretched length that is less than an unstretched length of the first transitioning compression region. According to certain embodiments, the first uniform compression region, the second uniform compression region, and the first transitioning compression region extend around a circumference of the compression article. However, in other embodiments, the first uniform compression region, the second uniform compression region, and the first transitioning compression region extend across a weft width direction of the compression article. In such embodiments, the compression article exerts radial compression across the weft width direction.

In accordance with certain embodiments, the compression article comprises a material having an elastic component and a relaxed component. Moreover, in some embodiments, an outer surface of the compression article comprises raised wales, and a skin surface of the compression article comprises a smooth surface. In further embodiments, the compression article is seamless.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A compression article, comprising:
   at least two uniform compression regions, including a first uniform compression region having a first compression pressure and a second uniform compression region having a second compression pressure; and
   at least one transitioning compression region, including a first transitioning compression region positioned between the first and second uniform compression regions, the first transitioning compression region comprising a first end adjacent or proximate to the first uniform compression region and a second end adjacent or proximate to the second uniform compression region;
      wherein the first transitioning compression region comprises a compression pressure gradient extending from the first end to the second end of the first transitioning compression region, wherein a magnitude of said compression pressure gradient is lower at a region adjacent to said first uniform compression region and at a second region adjacent to said second uniform compression region than a magnitude of said compression pressure gradient located between said first and second adjacent regions, and
      wherein the first uniform compression region comprises at least predominantly a first yarn, the second uniform compression region comprises predominantly a second yarn, wherein the first uniform compression region, the second uniform compression region, and the first transitioning compression region extend around a circumference of the compression article.

2. The compression article according to claim 1, wherein the first compression pressure and the second compression pressure each comprise from about 5 mmHg to about 40 mmHg.

3. The compression article according to claim 1, wherein the first compression pressure is greater than the second compression pressure.

4. The compression article according to claim 1, wherein the compression pressure gradient comprises a change in pressure from about 1% per inch to about 20% per inch.

5. The compression article according to claim 1, wherein the first uniform compression region and the second uniform compression region comprise different elastomeric yarns.

6. The compression article according to claim 5, wherein the elastomeric yarns comprise spandex.

7. The compression article according to claim 5, wherein the elastomeric yarns comprise from about 20 denier to about 150 denier.

8. The compression article according to claim 1, wherein the first end of the first transitioning compression region comprises a greater amount of the first yarn than the second yarn, and the second end of the first transitioning compression region comprises a greater amount of the second yarn than the first yarn.

9. The compression article according to claim 1, wherein the first transitioning compression region comprises from about 1% to about 50% of an unstretched length of the compression article.

10. The compression article according to claim 1, wherein the first uniform compression region and the second uniform compression region comprise from about 50% to about 99% of the unstretched length of the compression article.

11. The compression article according to claim 1, wherein the first transitioning compression region comprises an unstretched length from about 0.1 cm to about 50 cm.

12. The compression article according to claim 1, wherein at least one of the first uniform compression region and the second uniform compression region has an unstretched length that is greater than an unstretched length of the first transitioning compression region.

13. The compression article according to claim 1, wherein at least one of the first uniform compression region and the second uniform compression region has an unstretched length that is less than an unstretched length of the first transitioning compression region.

14. The compression article according to claim 1, wherein the first uniform compression region, the second uniform compression region, and the first transitioning compression region extend across a weft width direction of the compression article, and wherein the compression article exerts radial compression across the weft width direction.

15. The compression article according to claim 1, wherein the compression article comprises at least three uniform compression regions and at least two transitioning compression regions.

16. The compression article according to claim 1, wherein the compression article is seamless.

* * * * *